United States Patent [19]
Harrison et al.

[11] Patent Number: 5,948,470
[45] Date of Patent: *Sep. 7, 1999

[54] METHOD OF NANOSCALE PATTERNING AND PRODUCTS MADE THEREBY

[76] Inventors: Christopher Harrison, 807 Lake View Ter., Princeton, N.J. 08540; Miri Park, 8532 Town Ct. N., Laurenceville, N.J. 08648; Richard Register, 1 Sarah Dr., Princeton Junction, N.J. 08550; Douglas Adamson, 348 Grandview Rd., Skillman, N.J. 08558; Paul Mansky, 33 Meadow St., Apt. A, Amherst, Mass. 01002; Paul Chaikin, 121 Blackwell Rd., Pennington, N.J. 08534

[ * ] Notice: This patent issued on a continued prosecution application filed under 37 CFR 1.53(d), and is subject to the twenty year patent term provisions of 35 U.S.C. 154(a)(2).

[21] Appl. No.: 09/064,274

[22] Filed: Apr. 22, 1998

Related U.S. Application Data

[60] Provisional application No. 60/045,019, Apr. 28, 1997.
[51] Int. Cl.[6] ..................................................... B05D 5/00
[52] U.S. Cl. ...................... 427/198; 427/430.1; 156/659; 156/654; 156/656
[58] Field of Search .............................. 156/60, 628, 635, 156/638, 644, 654, 646.1, 654.1, 656.1, 659.11, 643, 646, 659.1, 630, 633, 657, 660, 667, 659, 656; 427/180, 183, 43.1, 189, 195, 197, 198, 220, 221, 272, 282, 430.1

[56] References Cited

U.S. PATENT DOCUMENTS

| | | | |
|---|---|---|---|
| 4,407,695 | 10/1983 | Deckman et al. | 156/643 |
| 4,512,848 | 4/1985 | Deckman et al. | 156/630 |
| 4,801,476 | 1/1989 | Dunsmuir et al. | 427/430.1 |

OTHER PUBLICATIONS

Chou, S., "Single–domain magnetic pillar array of 35 nm diameter and 65 Gbits/in.[2] density for ultrahigh density quantum magnetic storage", *J. Appl. Physics* 1994 76:6673.

Douglas et al., "Transfer of Biologically Derived Nanometer–Scale Patterns to Smooth Substrates", *Science* 1992 257:642.

Kryder, M.H., "Magnetic thin films for data storage", *Thin Solid Films* 1992 216:174.

Tonucci et al., "Nonochannel Array Glass", *Science* 1992 258:738.

Volkmuth, W.D. and Austin, R.P.H., "DNA electrophoresis in microlithographic arrays", *Nature* 1992 358:600 1992.

*Primary Examiner*—Merrick Dixon
*Attorney, Agent, or Firm*—Law Offices of Jane Massey Licata

[57] ABSTRACT

Methods of nanometer pattern formation and transfer onto a selected substrate are provided wherein a selected block copolymer is coated onto the selected substrate and a component of the block copolymer is chemically modified or physically removed so that the dense periodic pattern of the block copolymer can be transferred onto the selected substrate. Substrates prepared by these methods are also provided.

2 Claims, No Drawings

METHOD OF NANOSCALE PATTERNING AND PRODUCTS MADE THEREBY

This application claims benefit of provisional Appln. 60/045,019 filed Apr. 28, 1997.

This invention was made in the course of research sponsored by the National Science Foundation. The U.S. Government may have certain rights in this invention.

BACKGROUND OF THE INVENTION

Because of the drive toward smaller, faster and denser microelectronic systems, a number of different techniques for nanolithography have been investigated. In general, feature sizes greater than 200 nm can be routinely produced by photolithography techniques. Electron beam lithography is commonly used to access length scales below that of photolithography, i.e., 200 nm down to 30 nm. However, feature sizes less than 30 nm are not easily obtained by standard semiconductor lithography techniques.

Techniques currently used for the fabrication of small structures on planar substrates are broadly classified as serial (one feature is created at a time) or parallel (an entire pattern or structure is made in a single step). Photolithography, the most commonly used technique in the microelectronics industry, falls into both categories. In this process, a mask is first prepared by a serial technique, which contains a highly specific and detailed pattern. The pattern contained in the mask can then be transferred in parallel (in a single step) to a substrate (e.g., a silicon wafer), by a photographic exposure and developing process. The minimum feature sizes attainable are typically 200 nm at present, and are determined by the wavelength of light used in the exposure, and the chemical properties of the substrate.

Serial techniques include electron beam lithography, and more recently, lithography based on scanned probes (scanning tunnelling microscope, scanning force microscope, etc.). These offer the advantage of feature sizes as small as 20 nm for electron beam processes. These techniques offer precise control of feature placement. However, they are extremely slow due to their serial nature, and are best applied either to the fabrication of masks for subsequent parallel exposure, or to the fabrication of small numbers of devices for research or specialty applications.

Several methods have also recently been proposed which use a printing or stamping process to transfer small features which have been fabricated initially by a high resolution serial technique.

In addition, U.S. Pat. No. 4,512,848 discloses a process wherein an intermediate transfer mask consisting of a polymer is used to copy a master pattern. The intermediate transfer mask is then separated from the master pattern and placed on the surface of a substrate so as to form a lithographic mask. The pattern derived from the lithographic mask is then transferred to a substrate by etching.

An alternative strategy for nanoscale patterning is to use a "naturally occurring" or "self-assembling" structure as a template for subsequent parallel fabrication. For example, Deckman and Dunsmuir used a spin coating technique to prepare close-packed monolayers or colloidal polystyrene spheres with diameters of typically 0.1–10 microns on solid substrates. U.S. Pat. No. 4,407,695 and U.S. Pat. No. 4,801, 476. The pattern is then replicated by a variety of techniques, including evaporation through the interstices, ion milling of the spheres and/or the substrates, and related techniques. Clark and Douglas used highly ordered biologically membranes ("S-layers") as starting points for fabrication, and processed these by techniques such as evaporation at a glancing angle and ion milling (Douglas et al. *Science* 1992 257:642). Close packed bundles of cylindrical glass fibers, which could be repeatedly drawn and repacked to reduce the diameters and lattice constant have also been used (Tonucci et al. *Science* 1992 258:738). Block copolymer films have also been suggested for use as lithography masks wherein micelles of the copolymer which form on the surface of a water bath are subsequently picked up on a substrate. Contrast comes from variations in the initial film thickness as formed on the water surface.

In general, techniques of this nature have both advantages and disadvantages. The potential advantages are (1) production of extremely regular arrays of features, with uniform size and spacing, on length scales which are difficult to access by e-beam lithography, and (2) their production in an extremely rapid, parallel fashion, over essentially unlimited large areas. The disadvantage is chiefly the restriction to a very limited number of patterns.

Accordingly, methods are needed for efficient, uniform nanometer periodic pattern formation and transfer to substrates which are suitable for various technological applications.

SUMMARY OF THE INVENTION

An object of the present invention is to provide methods of nanometer pattern formation and transfer onto selected substrates. In these methods, a block copolymer having a dense, periodic pattern with a feature size of less than 100 nm is selected. A thin film of the selected block copolymer is then coated onto a selected substrate and a component of the block copolymer is chemically altered and/or physically removed. The dense periodic pattern of the block copolymer is then transferred onto the selected substrate.

Another object of the present invention is to provide a substrate having a dense periodic pattern with a feature size of less than 100 nm, said substrate being produced by transfer of this pattern from a block copolymer thin film coated on the substrate.

DETAILED DESCRIPTION OF THE INVENTION

In the present invention, a method is provided for nanometer pattern formation and transfer onto selected substrates. This process opens a route for nanometer-scale surface patterning by utilizing spontaneous self-assembly in synthetic materials at length scales difficult to obtain by standard semiconductor lithography techniques. The method of the present invention is completely different to standard techniques such as photolithography, e-beam lithography, scanned probe-based lithography, imprint lithography, and microcontact printing and provides a number of advantages over these techniques. Advantages of this technique include production of small, uniform, feature sizes typically ranging from 5 to 100 nm at a high density, typically $10^{10}$ to $10^{12}$ dots per $cm^2$, $10^5$ to $10^6$ lines per cm, at regularly spaced intervals, i.e., hexagonally close packed layers of dots or parallel and uniformly spaced lines. This method provides an easy means for pattern transfer over large areas.

In this method, a block copolymer having a nanometer pattern is selected as a template or mask. A thin film of the block copolymer is coated onto a selected substrate. A selected component of the block copolymer is then chemically altered or modified and/or physically removed from the coating and the nanometer pattern of the block copolymer is then transferred to the selected substrate.

By substrate it is meant to include, but is not limited to, commonly used semi-conductor substrates which can be patterned by the method of the present invention. Examples include, but are not limited to, silicon and germanium. In addition, the present invention's patterning is applicable to insulators such as silicon nitride and silicon oxide. Further, by substrates, it is meant to include metals such as, but not limited to, tungsten and molybdenum which can be patterned by this technique.

After patterning one of these substrates by the method of the present invention, the pattern of the substrate can be used to pattern a third layer in a typical trilayer patterning process. For example, the polymer mask can be used to pattern silicon nitride deposited upon a layer of polyimide. Because of the higher etching rate of polyimide as compared to silicon nitride under oxygen reactive ion etching, structures with large aspect ratios can be produced in the polyimide and then transferred to the substrate underneath.

Block copolymers consist of amphiphilic components which are attached by covalent bonding. Examples include, but are not limited to, linear diblock, triblock, and multiblock copolymers, star copolymers, and graft copolymers. Because of the incompatibility between the polymer molecules and connectivity constraints, block copolymers spontaneously self-assemble into microphase-separated nanometer size domains that exhibit ordered morphologies at equilibrium. In a given block copolymer system, the relative chain lengths of the blocks determine the resulting morphology. Commonly observed microdomain morphologies in bulk samples include periodic arrangements of lamellae, cylinders, and spheres. The sizes and periods of these microdomain structures are governed by the chain dimensions and are typically on the order of 10 nm. Sub-10 nm structures are also obtainable by choosing appropriate blocks with a high Flory-Huggins interaction parameter and decreasing the block lengths. Ordered structures can form in any block copolymer which has sufficient incompatibility between the blocks (determined by the degree of polymerization N, the Flory-Huggins interaction parameter $\chi$, and the copolymer architecture and block lengths).

Recent work with block copolymer thin films has shown them to be useful as templates or masks in nanolithography. It has now been found that blocks can be selected to optimize both the structure or pattern of the film and its processability or ease of use for pattern transfer onto selected substrates.

Various dense, nanometer patterns with a periodic in-plane structure can be produced from the block copolymers by a number of means. For example, parallel lines can be produced either by a film of lamellae which are oriented normal to a substrate or by a monolayer of cylinders which lie parallel to a substrate. Alternatively, arrays of dots can be produced using cylinders standing on end or using a monolayer of spheres. For films produced on uniform substrates, the periodic ordering produced has a polycrystalline character; that is, the surface contains regular arrays with a single orientation over typically several tens of lattice constants, but the surface is covered with grains with different orientations.

A thin film of the block copolymer is then coated onto a selected substrate, once an appropriate composition of the polymer is selected, and the correct film thickness and wetting conditions are determined. Means of production of thin films of block copolymers include, but are not limited to, quiescent evaporation and Langmuir films. Langmuir films can be coated onto various substrates. However, it is difficult to uniformly coat substrates with these films. In a preferred embodiment, spin coating is used to coat the thin film onto the substrate. Spin coating provides a rapid means for producing uniform and reproducible thin films of block copolymers over large areas (many $cm^2$) of a selected substrate.

To make a useful mask, typically a selected component of the block copolymer thin film is physically removed or chemically modified. The means of alteration is routinely selected by one of skill in the art in accordance with the components of the block copolymer. The following embodiments are provided for illustrative purposes only and are not meant to limit the method of the present invention.

In one embodiment, a first component of the block copolymer is a polymer which is strongly resistant to a particular reactive ion etching process (RIE), while a second component of the block copolymer is easily etched by the same process. In this embodiment, simple exposure to an anisotropic etching process will remove the second component preferentially, eventually reaching the substrate. Regions covered by domains of the first component will be protected. An example of such a block copolymer is poly (styrene-block-dimethylsiloxane) (PDMS), P(S-b-DMS). PDMS has strong resistance to many types of reactive ion etch processes, while polystyrene (PS) does not.

In another embodiment, a first component of a block copolymer may have a response to radiation. For example, if a first component of the block copolymer becomes degraded upon exposure to radiation (i.e., undergoes chain scission) while a second component of the block copolymer is left unaffected or is cross-linked, then the first component can be removed by this method, leaving behind the second component, which maintains its original structure or pattern. Types of radiation which can be used include electromagnetic radiation (light/x-rays), electron beams, beams of nuclear particles, etc. For example, it is known that poly (methylmethacrylate) (PMMA) can be degraded effectively by exposure to an electron beam or ultraviolet light, while PS is much more stable.

In yet another embodiment, selective chemistry is used to remove one component block. In this embodiment, if a first component of a block copolymer is chemically degraded by exposure to substance C, while a second component of a block copolymer is unaffected or cross-linked, then treatment of the film by substance C can be used to remove the first component and leave behind the patterned matrix of the second component. For example, it has now been demonstrated that the polybutadiene component of a P(S-b-B) block copolymer can be removed by reaction with ozone in an aqueous environment, while PS is cross linked.

Selective chemistry can also be used to chemically modify one or more block copolymer components to alter their etching rate. Various means to selectively, chemically modify one or more block copolymers are known. For example, the polyisoprene (PI) or polybutadiene (PB) component of a PI-PS or PB-PS is selectively modified with vapors of osmium tetroxide, an aggressive staining agent that deposits osmium tetroxide on the diene carbon-carbons double bonds. This heavy metal reduces the etch rate of the diene component in a 10:1 $CF_4:O_2$ plasma. The PS etches twice as fast as the PB or PI component and the pattern is transferred to the substrate.

Once the polymer film has been suitably coated on the substrate and/or modified, the pattern can be transferred to the substrate by a variety of means. For example, an etching process can be used to remove substrate material beneath the regions from which polymer was removed, while leaving the material under the protected regions unaffected. Examples of etching process which may be used include, but are not limited to, reactive ion etching, ion milling and wet chemical etching.

Alternatively, instead of removing substrate material, another material can be selectively deposited on the substrate in regions left exposed by previous etching, again following the pattern of the copolymer film's domain structure. The remaining polymer can be left in place or removed. Deposition techniques which may be used include, but are not limited to: evaporation (thermal, electron beam, etc.); sputtering; chemical vapor deposition; molecular beam epitaxy; chemical or physical adsorption of substances from solution to exposed region of the substrate, including small molecules, macromolecules, proteins, self-assembled monolayers, colloidal particles of various substances, etc; and electroplating and other electrodeposition techniques.

As will be obvious to those of skill in the art upon this disclosure, other physical or chemical processes, devices, or methodologies which replicate or couple the domain structure of a block copolymer film into another physical or chemical system can also be used in this invention.

There are a multitude of applications for substrates having nanometer periodic patterning produced by the method of the present invention. For example, films consisting of regular arrays of magnetic particles (of any shape or aspect ratio) can be produced using the above methods. These can be used for storage of information in a variety of ways. One bit of information can be encoded in the magnetization of a single magnetic particle, via the direction of that particles magnetization. The means for the storage and retrieval of information and use a single particle for each bit is well known in the art. In addition to "one bit per dot" storage, the method of the present invention can be used to produce a high density of small, uniformly sized, weakly coupled particles, which can be used in aggregate to store data with high density and low noise in the same way the polycrystalline magnetic films are currently used (Kryder, M. H. *Thin Solid Films* 1992 216:174; Chou, S. J. *Appl. Physics* 1994 76:6673).

In addition, quantum dots have been proposed by many researchers as useful structures for producing and controlling light in semiconductors and other materials. Quantum confinement can produce changes in the energy levels, density of states, and the selection rules and rates for electron/hole recombination of a given material, which can greatly enhance a material's suitability for light emission (photoluminescence, electroluminescence, lasing). Using the method of the present invention, arrays of quantum dots can be produced having a high density, uniform size, and regular spacing. The quantum dots can be produced rapidly (each production step being performed in parallel) and inexpensively over large areas, using the method of the present invention in conjunction with other lithography techniques or molecular beam epitaxy. Other advantages of this method include narrower line widths and greater intensity/efficiency.

In addition, porous structures in silicon have recently been shown to be extremely promising, in that they increase the efficiency of visible light emission from silicon by many orders of magnitude. However, the pore geometry is poorly controlled and the emission mechanism is not fully understood. Using the method of the present invention, however, structures consisting of columnar pores of uniform size and spacing can be produced in silicon or other materials so that this emission mechanism can be better studied and controlled.

The method of the present invention can also be used to transfer a nanometer pattern to a thin inorganic film to produce a close-packed array of monodisperse, nanometer sized pores, which penetrate from the top to the bottom of the inorganic film. Such a structure can be used as a filter membrane for applications such as ultrafiltration, reverse osmosis, dialysis, and other separation processes, and has the combined advantages of small pore size, uniform pore size and high pore density. In addition, the polymer template pattern could be used to seed the growth of inorganic aluminum oxide membrane filters.

In addition, Austin et al. have recently proposed the use of columnar structures or "mazes" in silicon as a controlled means of separating DNA fragments by length (Volkmuth, W. D. and Austin, R. P. H. *Nature* 1992 358:600 1992). The method of the present invention could be used to produce such arrays on a length scale of 5–100 nm, where their utility in such separations is expected to be much greater.

Other chromatographic techniques wherein the method can be used include the patterning of walls of a long capillary with regular arrays of pores or beads which fill a column. Various physical/chemical phenomena can then lead to separation of molecules passing through the column by size, due to preferential filling and retention rates of different Mw particles in the regular pores. The uniformity of the pore sizes will make the separation more precise.

In addition, the method of the present invention can be used to produce regular arrays of binding/adsorption sites on a substrate for the binding or immobilization of proteins or other molecules on well defined sites. Regular arrays of nucleation sites on a substrate can also be produced, for controlling subsequent inorganic or organic film growth. For example, recent work has shown the feasibility of selective deposition of barium titanate in the diene component of block copolymer thin films. Film morphology can be controlled by texturing of the substrate prior to deposition. In addition, the surface area of an inorganic film can be greatly increased by this patterning technique, with excellent control of the surface morphology.

In addition, substrate produced in accordance with the method of the present invention can be used as nanometer calibration samples for electron microscopy. Further, with proper control of the orientation of the cylindrical microstructure, a sufficient pattern can be made and transferred to a substrate to produce an X-ray diffraction grading.

As will be obvious to those of skill in the art, while specific applications are mentioned as examples of the utility of the invention, the patent is not limited to these, but is meant to cover any useful structures which can be made by the processes described herein.

The following nonlimiting examples are provided to further illustrate the present invention.

EXAMPLES

Example 1

Patterning a Silicon Nitride Substrate with PS-PB or PS-PI templates

Using the method of the present invention, dense periodic arrays of holes or dots were fabricated in a thin film of silicon nitride deposited on a silicon wafer. The holes or dots are 20 nanometers across, 40 nanometers apart, and hexagonally ordered with a polygrain structure having an average grain size of 10 by 10. In this embodiment, spin-coated block copolymer thin films with well-ordered spherical or cylindrical microdomains comprising asymmetric PS-PB or PS-PI were used as the templates.

Asymmetric PS-PB and PS-PI diblock copolymers were synthesized (designated SB 36/11 and SI 68/12, respectively, with the approximate molecular weights of the blocks given in kilograms per mole). In bulk, SB 36/11 microphase separates into a cylindrical morphology and produces hexagonally ordered PB cylinders embedded in PS matrix; SI 68/12 adopts a spherical morphology and produces PI spheres in PS matrix with body centered cubic order. Thin polymer films were produced by spin-coating polymer solutions in toluene onto silicon nitride, and the film thickness was controlled by varying spinning speed and polymer concentration. The films were annealed at 125° C., a temperature above their glass transition temperatures, for 24 hours in vacuum to obtain well-ordered morphologies.

To pattern the whole substrate, a uniform microdomain monolayer was produced over the substrate area in a controlled manner. Secondary ion mass spectroscopy confirmed that continuous PB wetting layers exist at both the air and silicon nitride interfaces for a PS-PB diblock copolymer film. The microdomain monolayer thickness was approximately 50 nm, including the wetting layers. It was found that by spin-coating at this thickness, a uniform template can be routinely obtained over the entire sample area.

A fluorine-based reactive ion etching (RIE) technique was used to transfer the microdomain pattern in the monolayer to the underlying silicon nitride with the copolymer film itself as the etching mask. The unaltered microphase separated PS-PB film alone does not produce a usable RIE mask because the etching rates of the PS and PB microdomains are almost the same under most RIE conditions. To transfer the pattern, a selective etching or masking between dissimilar microdomain regions is essential. Accordingly, the microdomain monolayer film was exposed to ozone to selectively degrade and remove the PB spherical domains prior to a $CF_4$ RIE or $CF_4/O_2$ RIE. Ozone predominantly attacks the carbon-carbon double bonds in the PB backbone, cutting the bonds and producing PB fragments that can be dispersed in water. This results in regular spherical voids in the PS matrix, and hence a variation of the effective total thickness of the copolymer mask. The regions underneath the empty spheres are protected by a thinner PS mask than the rest of the area and therefore can be exposed to the RIE while the rest is still protected to produce holes in silicon nitride.

A different processing technique was used to fabricate dots, instead of holes, in silicon nitride from the same spherical microdomain monolayer template. In this embodiment, $CF_4/O_2$ RIE was used and etching selectivity achieved by staining the PB domains with osmium tetroxide. Exposing the copolymer films to $OsO_4$ vapor resulted in a selective staining of PB because osmium adds across the carbon-carbon double bonds in the PB backbone. Osmium staining reduces the etching rate of the PB domains during the $CF_4/O_2$ RIE, producing an etching selectivity of PS to stained PB of approximately 2:1. Hence, the regions underneath the PB domains are partially masked from the RIE process, resulting in the fabrication of dots. Electron beam exposure done on the sample during the examination of the monolayer template prior to the etching process appears to enhance the contrast of the transferred microstructures. Pattern transfer was performed on thin silicon nitride membranes supported by a silicon wafer for observation by transmission electron microscopy.

These pattern transfer techniques were also applied to produce lines by using a monolayer of cylindrical microdomains as the template. In thin films, cylindrical microdomains generally lie parallel to the substrate and form a fingerprint-like pattern. Accordingly, with this template, finger-print like troughs are produced by the ozone technique, while lines are produced by the stained technique.

Observations with a scanning electron microscope also were made for a spherical phase copolymer, spin-coated and processed on a silicon nitride coated silicon wafer. A uniform spherical microdomain monolayer film was obtained from SI 68/12, a spherical PS-PI block copolymer. With this copolymer, the thickness of a microdomain monolayer was approximately 90 nm, and a uniform template of ordered PI spheres was routinely produced over an entire 3 inch wafer. The 2D microdomain morphology in the copolymer template on a thick substrate was directly imaged by an SEM technique combined with a non-selective RIE. This technique allows one to depth-profile copolymer films with approximately 10-nm depth resolution. For the film processing steps discussed herein, PI blocks behave similarly to PB blocks. The PI blocks also wet the air and silicon nitride interfaces, and any selective processing performed on PS-PB copolymer films can also be performed on PS-PI copolymer films. An SEM micrograph showed periodic arrays of holes in a silicon nitride covered silicon wafer. The pattern was transferred to the silicon nitride layer from an ozonated SI spherical monolayer film. The typical size of the arrays was 10 by 10 microstructures. The period of the holes is 40 nm, resulting a density of $7 \times 10^{10}$ holes per $Cm^2$. Using this method, similar structures have been fabricated uniformly over an area as large as a 3 inch wafer, drilling $3 \times 10^{12}$ holes into a silicon wafer.

What is claimed is:

1. A method of nanometer pattern formation and transfer onto a selected substrate comprising:

(a) selecting a block copolymer having a dense, periodic pattern with a feature size of less than 100 nm;

(b) coating the selected block copolymer onto a selected substrate;

(c) exposing the coated block copolymer on the selected substrate to ozone and physically removing a component of the block copolymer; and (d) transferring a pattern reflective of chemical modification and physical removal of the component of the block copolymer in step (c) onto the selected substrate.

2. A substrate having a dense periodic pattern with a feature size of less than 100 nm, said substrate being produced by method of claim 1.

* * * * *